US010059993B2

(12) United States Patent
Fiss et al.

(10) Patent No.: US 10,059,993 B2
(45) Date of Patent: Aug. 28, 2018

(54) OLIGONUCLEOTIDES FOR CONTROLLING AMPLIFICATION OF NUCLEIC ACIDS

(71) Applicant: Roche Molecular Systems, Inc., Pleasanton, CA (US)

(72) Inventors: Ellen H. Fiss, Albany, CA (US); Nicolas Newton, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 138 days.

(21) Appl. No.: 14/837,931

(22) Filed: Aug. 27, 2015

(65) Prior Publication Data

US 2016/0060694 A1 Mar. 3, 2016

(30) Foreign Application Priority Data

Aug. 28, 2014 (EP) .................................... 14182730

(51) Int. Cl.

*C12Q 1/68* (2018.01)
*C12Q 1/6876* (2018.01)
*C12Q 1/6851* (2018.01)

(52) U.S. Cl.

CPC ......... *C12Q 1/6876* (2013.01); *C12Q 1/6851* (2013.01); *C12Q 2600/166* (2013.01)

(58) Field of Classification Search

None

See application file for complete search history.

(56) References Cited

U.S. PATENT DOCUMENTS

| | | | |
|---|---|---|---|
| 8,609,340 | B2 | 12/2013 | Eickhoff et al. |
| 2012/0064511 | A1 | 3/2012 | Leying et al. |

FOREIGN PATENT DOCUMENTS

| | | | | |
|---|---|---|---|---|
| EP | 2426222 | A1 | 3/2012 | |
| EP | 2759604 | A2 | 7/2014 | |
| EP | 2759604 | A3 | 7/2014 | |
| WO | 2009117537 | A1 | 9/2009 | |
| WO | 2012013734 | A1 | 2/2012 | |
| WO | WO 2012013732 | A1 * | 2/2012 | ................ B01L 3/00 |

OTHER PUBLICATIONS

Nolan et al. (Quantification of mRNA using real-time RT-PCR, Nature Protocols, vol. 1, No. 3, Nov. 9, 2006).*

Untergasser et al. (Primer3Plus, an enhanced web interface to Primer3, Nucleic Acids Research, 2007, vol. 35, 2007).*

Rozen et al. (Primer3 on the WWW for General Users and for Biologist Programmers, in Methods in Molecular Biology, vol. 132: Bioinformatics Methods and Protocols, 2000)).*

Meng, et al., 2010, "A novel duplex real-time reverse transcriptase-polymerase chain reaction assay for the detection of hepatitis C viral RNA as internal control", Virology Journal, 7:117.

2009, "cobas TM TaqScreen MPX Test for use on the cobas s 201 system", p. 1-60.

Huang J., et al., 2008, "A Novel Real-time Multiplex Reverse Transcrptase-Polymerase Chain Reaction for the Detection of HIV-1 RNA by Using Dual-Specific Armored RNA as Internal Control", Intervirology, 51:42-49.

* cited by examiner

*Primary Examiner* — Aaron A Priest

(74) *Attorney, Agent, or Firm* — David J. Chang; Jeffery P. Bernhardt

(57) ABSTRACT

Methods and oligonucleotides are provided for detecting an internal control nucleic acid for qualitative and/or quantitative purposes.

12 Claims, 1 Drawing Sheet

Specification includes a Sequence Listing.

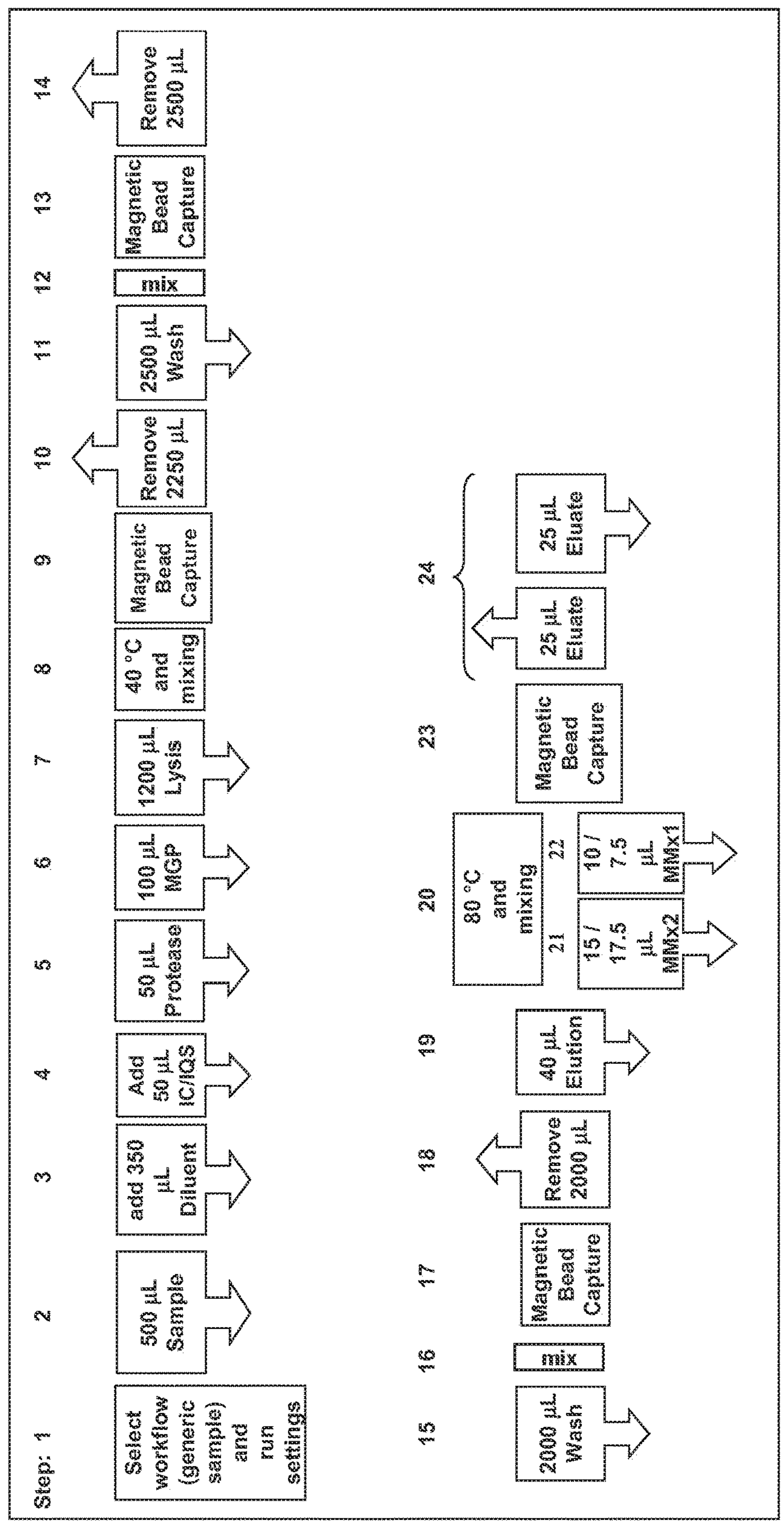
Step: 1
Select workflow (generic sample) and run settings
2
500 µL Sample
3
add 350 µL Diluent
4
Add 50 µL IC/IQS
5
50 µL Protease
6
100 µL MGP
7
1200 µL Lysis
8
40 °C and mixing
9
Magnetic Bead Capture
10
Remove 2250 µL
11
2500 µL Wash
12
mix
13
Magnetic Bead Capture
14
Remove 2500 µL
15
2000 µL Wash
16
mix
17
Magnetic Bead Capture
18
Remove 2000 µL
19
40 µL Elution
20
80 °C and mixing
21
15 / 17.5 µL MMx2
22
10 / 7.5 µL MMx1
23
Magnetic Bead Capture
24
25 µL Eluate
25 µL Eluate

OLIGONUCLEOTIDES FOR CONTROLLING AMPLIFICATION OF NUCLEIC ACIDS

CROSS REFERENCE TO RELATED APPLICATIONS

The present application claims the benefit under 35 U.S.C. § 119 of European Patent Application No. 14182730.3 filed on Aug. 28, 2014. The entire disclosure of the above-referenced prior application is hereby incorporated by reference in its entirety.

FIELD OF THE INVENTION

The present invention belongs to the field of in-vitro diagnostics. Within this field, it particularly concerns the amplification and detection of a control nucleic acid for qualitative and/or quantitative purposes.

BACKGROUND

In the field of molecular diagnostics, the amplification of nucleic acids from numerous sources has been of considerable significance. Examples for diagnostic applications of nucleic acid amplification and detection are the detection of viruses such as Human Papilloma Virus (HPV), West Nile Virus (WNV) or the routine screening of blood donations for the presence of Human Immunodeficiency Virus (HIV), Hepatitis-B (HBV) and/or C Virus (HCV). Furthermore, said amplification techniques are suitable for bacterial targets such as mycobacteria, or the analysis of oncology markers.

The most prominent and widely-used amplification technique is Polymerase Chain Reaction (PCR). Other amplification reactions comprise, among others, the Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification.

Automated systems for PCR-based analysis often make use of real-time detection of product amplification during the PCR process in the same reaction vessel. Key to such methods is the use of modified oligonucleotides carrying reporter groups or labels.

It has been shown that amplification and detection of more than one target nucleic acid in the same vessel is possible. This method is commonly termed "multiplex" amplification and requires different labels for distinction if real-time detection is performed.

It is mostly desirable or even mandatory in the field of clinical nucleic acid diagnostics to control the respective amplification using control nucleic acids with a known sequence, for qualitative (performance control) and/or quantitative (determination of the quantity of a target nucleic using the control as a reference) purposes. Given the diversity especially of diagnostic targets, comprising prokaryotic, eukaryotic as well as viral nucleic acids, and given the diversity between different types of nucleic acids such as RNA and DNA, control nucleic acids are usually designed in a specific manner.

EP 2759604 discloses a method for detection of a set of non-competitive internal control nucleic acids.

Described herein are improved oligonucleotides and methods for this purpose.

DESCRIPTION

A first aspect described herein is an isolated oligonucleotide with the sequence of SEQ ID NO 1. This oligonucleotide can be used as a probe for the improved detection of a control nucleic acid comprising the sequence of SEQ ID NO 4.

Thus, another aspect described herein is a use of a probe with SEQ ID NO 1 for the detection of a control nucleic acid comprising SEQ ID NO 4.

The sequence of SEQ ID NO 4 is a scrambled sequence not showing any significant homology to any naturally occurring sequences, such that it may serve as a non-competitive internal control nucleic acid sequence for qualitative and/or quantitative detection of multiple target nucleic acids, as described in EP 2759604.

In nucleic acid amplification assays such as, for instance, PCR assays like real-time PCR assays, SEQ ID NO 4 can be efficiently amplified with a specific set of primers comprising a first primer with SEQ ID NO 2 and a second primer with SEQ ID NO 3.

Hence, an aspect described herein is a composition comprising the oligonucleotides with the SEQ ID NOs 1, 2 and 3.

These nucleic acids may be provided to the skilled person as a kit-of-parts, further comprising a suitable amplification and detection target, namely a control nucleic acid with the sequence of SEQ ID NO 4.

Therefore, a further aspect described herein is a kit for controlling the detection of multiple target nucleic acids, the kit comprising a detection probe with SEQ ID NO 1, a pair of amplification primers with SEQ ID NO 2 and SEQ ID NO 3, and a control nucleic acid comprising SEQ ID NO 4.

The use of a control nucleic acid comprising the sequence of SEQ ID NO 4 with the improved detection by a probe with SEQ ID NO 1 as described herein facilitates the development of improved simultaneous assays on a plurality of parameters and/or nucleic acid types while using the same internal control nucleic acid sequence for said different parameters and/or nucleic acid types. Therefore, it contributes to reducing the overall complexity of the corresponding experiments on various levels: For instance, only one internal control nucleic acid sequence has to be designed and added to the respective amplification mixes, thus saving the time and costs for designing and synthesizing or buying multiple control nucleic acid sequences. The assay or assays can be streamlined, and the risk of handling errors is reduced. In addition, the more different control nucleic acid sequences are employed in one assay or parallel assays that may be carried out simultaneously under the same conditions, the more complex it may result to adjust the respective conditions. Moreover, with a single control suitable for a plurality of nucleic acids, said control can be dispensed from a single source into different vessels containing said different target nucleic acids. In some embodiments, the single control nucleic acid sequence may also serve as a qualitative and as a quantitative control.

The improvement of the detection of a control nucleic acid comprising SEQ ID NO 4 by using a probe with the sequence of SEQ ID NO 1, as shown in the Example herein, enhances the reliability of the measurements carried out according to the method described in EP 2759604. The probe with the sequence of SEQ ID NO 1 does not overlap with any oligonucleotide sequences disclosed in EP 2759604, in particular not with the probe with the sequence of SEQ ID NO 5 (disclosed as SEQ ID NO 52 in EP 2759604) against which SEQ ID NO 1 has been tested in the current Example.

A process in which the use of a control nucleic acid comprising the sequence of SEQ ID NO 4 with the improved detection by a probe with SEQ ID NO 1 can be advantageously applied is the following:

A process for internally controlled isolating and simultaneously amplifying a first and a second target nucleic acid that may be present in one or more fluid samples, said process comprising the automated steps of:

a. adding an internal control nucleic acid comprising the sequence of SEQ ID NO 4 to each of said fluid samples
b. combining together a solid support material and said one or more fluid samples in one or more vessels for a period of time and under conditions sufficient to permit nucleic acids comprising the target nucleic acids, if present on said one or more fluid samples, and the internal control nucleic acid to be immobilized on the solid support material
c. isolating the solid support material from the other material present in the fluid samples in a separation station
d. purifying the nucleic acids in said separation station and washing the solid support material one or more times with a wash buffer
e. contacting the purified target nucleic acids and the purified internal control nucleic acid with amplification reagents comprising a distinct set of primers and a probe for each of said target nucleic acids and a set of primers comprising a first primer with SEQ ID NO 2 and a second primer with SEQ ID NO 3 and a probe with SEQ ID NO 1 for said internal control nucleic acid in at least two reaction vessels, wherein a first reaction vessel comprises primers and a probe for said first target nucleic acid and at least a second reaction vessel comprises primers and a probe for said second target nucleic acid and wherein the primers and the probe for the first target nucleic acid are absent from the second reaction vessel and the primers and the probe for the second target nucleic acid are absent from the first reaction vessel
f. incubating in said reaction vessels said purified target nucleic acids and said purified internal control nucleic acid with said amplification reagents for a period of time and under conditions sufficient for an amplification reaction indicative of the presence or absence of said target nucleic acids to occur
g. detecting and measuring signals generated by the amplification products of said target nucleic acids and being proportional to the concentration of said target nucleic acids, and detecting and measuring a signal generated by said internal control nucleic acid, wherein the conditions for amplification and detection in steps d. to g. are identical for the first and the second reaction vessel and thus for the target nucleic acids and the internal control nucleic acid.

As one of the advantages of the process described herein, the testing of a particular biological sample for other nucleic acids in possible subsequent experiments need not involve another sample preparation procedure with the addition of a different internal control nucleic acid, since the control comprising SEQ ID NO 4 can be used to control the amplification of different nucleic acids. Thus, once an internal control nucleic acid has been added, other parameters may be tested in the same sample under the same conditions.

The internal control nucleic acid described above is non-competitive.

A "non-competitive internal control nucleic" acid has different primer binding sites than the target and thus binds to different primers. Advantages of such a setup comprise, among others, the fact that the single amplification events of the different nucleic acids in the reaction mixture can take place independently from each other without any competition effects. Thus, no adverse effects occur regarding the limit of detection of the assay as can be the case in a competitive setup.

The fact that the process described herein involves a distinct set of primers for each of said target nucleic acids and for said internal control nucleic acid renders the method considerably flexible. In this non-competitive setup it is not necessary to introduce target-specific binding sites into the control nucleic acid as in the case of a competitive setup, and the drawbacks of a competitive setup, such as competition for amplification reagents, are avoided. In a non-competitive setup, the internal control nucleic acid has a sequence different from any target sequences, in order not to compete for their primers and/or probes. The sequence of the internal control nucleic acid is different from the other nucleic acid sequences in the fluid sample. As an example, if the fluid sample is derived from a human, the internal control nucleic acid does not have a sequence which also endogenously occurs within humans. The difference in sequence is thus at least significant enough to not allow the binding of primers and/or probes to the respective endogenous nucleic acid or acids under stringent conditions and thus render the setup competitive. SEQ ID NO 4 is a scrambled sequence originally based on a naturally occurring genome. As known in the art, "scrambling" means introducing a number of base mutations into a sequence. In the case of SEQ ID NO 4, the sequence of the internal control nucleic acid used in the invention is substantially altered with respect to the naturally occurring gene it is derived from.

The process comprising the automated steps as described herein also displays various additional advantages:

It has been a challenge in the prior art that the number of different target nucleic acids in a multiplex assay carried out in a single reaction vessel is limited by the number of appropriate labels. In a real-time PCR assay, for example, the potential overlap of fluorochrome spectra has a great impact on assay performance (risk of false positive results, lower precision etc.) Therefore, the respective fluorophores have to be carefully selected and spectrally well separated in order to assure the desired performance of a diagnostic test. Typically, the number of different usable fluorophores corresponds to a single-digit number of PCR instrument fluorescence channels.

In contrast, in the process described herein, the internally controlled amplification of at least a first and a second target nucleic acid takes place in at least two different reaction vessels, allowing for the simultaneous amplification of a higher number of different target nucleic acids, since signals in different reaction vessels can be detected independently from each other. Still, included herein are embodiments wherein in one or more of the multiple reaction vessels multiplex reactions are performed, thereby multiplying the number of targets that may be amplified simultaneously and under the same conditions. In such embodiments, the internal control nucleic acid serves as a control for the different target nucleic acids within a vessel as well as different target nucleic acids in different vessel.

Thus, in some embodiments of the process described herein, at least two target nucleic acids are amplified in the same reaction vessel.

Especially if a fluid sample is suspected to contain target nucleic acids from different organisms, or even the different organisms as such, or if it is not clear which of the different nucleic acids or organisms may be present in said sample, an embodiment is the process described herein, wherein the first target nucleic acid and the second target nucleic acid are from different organisms.

In an embodiment of the process described herein, the first and/or the second target nucleic acid is a viral nucleic acid.

In a further embodiment of the process described herein, the first and/or the second target nucleic acid is a non-viral nucleic acid.

In yet a further embodiment of the process described herein, the first and/or the second target nucleic acid is a bacterial nucleic acid.

As described before, the process described herein is useful for qualitatively or quantitatively controlling the amplification of at least a first and a second target nucleic acid.

Qualitative detection of a nucleic acid in a biological sample is, for instance, crucial for recognizing an infection of an individual. Thereby, one important requirement for an assay for detection of a microbial infection is that false-negative or false-positive results be avoided, since such results would almost inevitably lead to severe consequences with regard to treatment of the respective patient. Thus, especially in PCR-based methods, a qualitative internal control nucleic acid is added to the detection mix. Said control is particularly important for confirming the validity of a test result: At least in the case of a negative result with regard to the respective target nucleic acid, the qualitative internal control reaction has to perform reactive within given settings, i.e. the qualitative internal control must be detected, otherwise the test itself is considered to be inoperative. However, in a qualitative setup, said qualitative internal control does not necessarily have to be detected in case of a positive result. For qualitative tests, it is especially important that the sensitivity of the reaction is guaranteed and therefore strictly controlled As a consequence, the concentration of the qualitative internal control must be relatively low so that even in a situation of slight inhibition the qualitative internal control is not detected and therefore the test is invalidated.

Thus, in some embodiments of the process described herein, the presence of an amplification product of said internal control nucleic acid is indicative of an amplification occurring in the reaction mixture even in the absence of amplification products for one or more of said target nucleic acids.

On the other hand and in addition to mere detection of the presence or absence of a target nucleic acid in a sample, it is often important to determine the quantity of said nucleic acid. As an example, stage and severity of a viral disease may be assessed on the basis of the viral load. Further, monitoring of any therapy requires information on the quantity of a pathogen present in an individual in order to evaluate the therapy's success. For a quantitative assay, it is necessary to introduce a quantitative standard nucleic acid serving as a reference for determining the absolute quantity of a target nucleic acid. Quantitation can be effectuated either by referencing to an external calibration or by implementing an internal quantitative standard.

In the case of an external calibration, standard curves are created in separate reactions using known amounts of identical or comparable nucleic acids. The absolute quantity of a target nucleic acid is subsequently determined by comparison of the result obtained with the analyzed sample with said standard function. External calibration, however, has the disadvantage that a possible extraction procedure, its varied efficacy, and the possible and often not predictable presence of agents inhibiting the amplification and/or detection reaction are not reflected in the control.

This circumstance applies to any sample-related effects. Therefore, it might be the case that a sample is judged as negative due to an unsuccessful extraction procedure or other sample-based factors, whereas the target nucleic acid to be detected and quantified is actually present in the sample.

For these and other reasons, an internal control nucleic acid added to the test reaction itself is of advantage. When serving as a quantitative standard, said internal control nucleic acid has at least the following two functions in a quantitative test:

i) It monitors the validity of the reaction.

ii) It serves as reference in titer calculation thus compensating for effects of inhibition and controlling the preparation and amplification processes to allow a more accurate quantitation. Therefore, in contrast to the qualitative internal control nucleic acid in a qualitative test which must be positive only in a target-negative reaction, the quantitative control nucleic acid in a quantitative test has two functions: reaction control and reaction calibration. Therefore it must be positive and valid both in target-negative and target-positive reactions.

It further has to be suited to provide a reliable reference value for the calculation of high nucleic acid concentrations. Thus, the concentration of an internal quantitative control nucleic acid needs to be relatively high.

Therefore, in some embodiments, the process described herein further comprises the following step:

h. determining the quantity of one or more of said target nucleic acids.

The internally controlled process described herein requires considerably less hands-on time and testing is much simpler to perform than, for example, real-time PCR methods used in the prior art. The process offers a major advantage in the field of clinical virology as it permits parallel amplification of nucleic acids from several viruses like DNA and RNA viruses, bacteria, and/or other pathogens in parallel experiments. The process is particularly useful in the management of post-transplant patients, in whom frequent viral monitoring is required. Thereby said process facilitates cost-effective diagnosis and contributes to a decrease in the use of antiviral agents and in viral complications and hospitalizations. This equally applies to the field of clinical microbiology. In general, efficiencies will be gained in faster turnaround time and improved testing flexibility. Consequently, this leads to a decrease in the number of tests requested on a patient to make a diagnosis, and potentially shorter hospital stays (for example, if a diagnosis can be provided sooner, patients requiring antimicrobial therapy will receive it sooner and thus recover earlier). In addition, patients show less morbidity and therefore cause fewer costs related to supportive therapy (for example, intensive care related to a delay in diagnosis of sepsis). Providing a negative result sooner can have important implications for the overprescription of antibiotics. For example, if a test result obtained by the process according to the invention is able to rule out the pathogen more quickly than with a standard real-time PCR method, then the clinician will not be forced to use empirical antibiotics. Alternatively, if empirical antibiotics are used, the duration of the respective treatment can be shortened.

With respect to designing a specific test based on the process described herein, the skilled artisan will benefit from the following advantages:

a reduction in software complexity (leading to a reduced risk of programming errors)

focusing of assay development efforts on the chemistry optimization instead of the chemistry plus the instrument control parameters much more reliable system since a single process is always used and the hardware can be optimally designed to perform this protocol the skilled artisan performing the internally controlled process described above is provided with the flexibility to run multiple different assays in parallel as part of the same process cost reduction.

In the context described herein, the term "solid support" as used herein relates to any type of solid support to which the analyte is capable of binding, either directly and non-specifically by adsorption, or indirectly and specifically. Indirect binding may be by binding to a capture nucleic acid probe which is homologous to a target sequence of the nucleic acid of interest. Thus, using capture probes attached on a solid support, a target nucleic acid can be separated from non-target material, or non-target nucleic acid. Such a capture probe is immobilized on the solid support. Solid support material may be a polymer, or a composition of polymers. Other types of solid support material include magnetic silica particles, metal particles, magnetic glass particles, glass fibers, glass fiber filters, filter paper etc., while the solid support material is not limited to these materials.

"Immobilize", as used herein, means to capture objects such as nucleic acids in a reversible or irreversible manner. Particularly, "immobilized on the solid support material" means that the object or objects are associated with the solid support material for the purpose of their separation from any surrounding media, and can be recovered, for example, by separation from the solid support material at a later point. In this context, "immobilization" can comprise the adsorption of nucleic acids to glass or other suitable surfaces of solid materials as described supra. Moreover, nucleic acids can be immobilized specifically by binding to capture probes, wherein nucleic acids are bound to essentially complementary nucleic acids attached to a solid support by base-pairing. In the latter case, such specific immobilization leads to the predominant binding of target nucleic acids.

As used herein, "purification", "isolation" or "extraction" of nucleic acids relate to the following: Before nucleic acids may be analyzed in a diagnostic assay by amplification, they typically have to be purified, isolated or extracted from biological samples containing complex mixtures of different components. For the first steps, processes may be used which allow the enrichment of the nucleic acids. After the purification or isolation of the nucleic acids including the target nucleic acids from their natural surroundings, analysis may be performed via the simultaneous amplification and detection described herein.

"Simultaneously", as used herein, means that two actions, such as amplifying a first and a second or more nucleic acids, are performed at the same time and under the same physical conditions. In one embodiment, simultaneous amplification of the at least first and second target nucleic acids is performed in one vessel. In another embodiment, simultaneous amplification is performed with at least one nucleic acid in one vessel and at least a second nucleic acid in a second vessel, at the same time and under the same physical conditions, particularly with respect to temperature and incubation time wherein the internal control nucleic acid mentioned above is present each of said vessels.

"Target nucleic acid" is used herein to denote a nucleic acid in a sample which should be analyzed, i.e. the presence, non-presence and/or amount thereof in a sample should be determined.

The "first target nucleic acid" and the "second target nucleic acid" are different nucleic acids.

The term "fluid sample" refers to a material that may potentially contain an analyte of interest. The sample can be derived from any source, in particular any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The fluid sample subjected to the process described herein can be pretreated prior to use, such as preparing plasma from blood, diluting viscous fluids, lysis, or the like. Methods of treatment can involve filtration, distillation, concentration, inactivation of interfering components, the addition of reagents, and the like. A fluid sample may be used directly as obtained from the source or used following a pretreatment to modify the character of the sample. In some embodiments, an initially solid or semi-solid material is rendered liquid by dissolving or suspending it with a suitable liquid medium. The fluid sample is suspected to contain a certain target nucleic acid.

The term "reaction vessel" comprises, but is not limited to, tubes or the wells of plates such as microwell, deepwell or other types of multiwell plates, in which a reaction for the analysis of the fluid sample such as e.g. reverse transcription or a polymerase chain reaction takes place. The outer limits or walls of such vessels are chemically inert such that they do not interfere with the analytical reaction taking place within. Preferably, the isolation of the nucleic acids as described above is also carried out in a multiwell plate.

In this context, multiwell plates in analytical systems allow parallel separation and analyzing or storage of multiple samples. Multiwell plates may be optimized for maximal liquid uptake, or for maximal heat transfer. A preferred multiwell plate for use in the context of the present invention is optimized for incubating or separating an analyte in an automated analyzer. Preferably, the multiwell plate is constructed and arranged to contact a magnetic device and/or a heating device.

A "separation station" is a device or a component of an analytical system allowing for the isolation of the solid support material from the other material present in the fluid sample. Such a separation station can e.g. comprise, but is not limited to, a centrifuge, a rack with filter tubes, a magnet, or other suitable components. In a preferred embodiment of the invention, the separation station comprises one or more magnets. Preferably, one or more magnets are used for the separation of magnetic particles, preferably magnetic glass particles, as a solid support. If, for example, the fluid sample and the solid support material are combined together in the wells of a multiwell plate, then one or more magnets comprised by the separation station can e.g. be contacted with the fluid sample itself by introducing the magnets into the wells, or said one or more magnets can be brought close to the outer walls of the wells in order to attract the magnetic particles and subsequently separate them from the surrounding liquid.

A "wash buffer" is a fluid that is designed to remove undesired components, especially in a purification procedure. Such buffers are well known in the art. In the context of the purification of nucleic acids, the wash buffer is suited to wash the solid support material in order to separate the immobilized nucleic acid from any unwanted components.

The wash buffer may, for example, contain ethanol and/or chaotropic agents in a buffered solution or solutions with an acidic pH without ethanol and/or chaotropic agents. Often the washing solution or other solutions are provided as stock solutions which have to be diluted before use.

For downstream processing of the isolated nucleic acids, it can be advantageous to separate them from the solid support material before subjecting them to amplification.

An "elution buffer" as used herein is a suitable liquid for separating the nucleic acids from the solid support. Such a liquid may be distilled water or aqueous salt solutions, such as Tris buffers like Tris HCl, or HEPES, or other suitable buffers known to the skilled artisan. The pH value of such an elution buffer is in some embodiments alkaline or neutral. Said elution buffer may contain further components such as chelators like EDTA, which stabilizes the isolated nucleic acids by inactivation of degrading enzymes.

"Amplification reagents", in the context of the invention, are chemical or biochemical components that enable the amplification of nucleic acids. Such reagents comprise, but are not limited to, nucleic acid polymerases, buffers, mononucleotides such as nucleoside triphosphates, oligonucleotides e.g. as oligonucleotide primers, salts and their respective solutions, detection probes, dyes, and more.

"Oligonucleotides" and "modified oligonucleotides" are components formed from a plurality of nucleotides as their monomeric units. The phosphate groups are commonly referred to as forming the internucleoside backbone of the oligonucleotide. The normal linkage or backbone of RNA and DNA is a 3' to 5' phosphodiester linkage. Methods for preparing oligomeric compounds of specific sequences are known in the art, and include, for example, cloning and restriction of appropriate sequences and direct chemical synthesis. In the process described above, the oligonucleotides may be chemically modified, i.e. the primer and/or the probe comprise a modified nucleotide or a non-nucleotide compound. The probe or the primer is then a modified oligonucleotide.

The term "primer" is used herein as known to the expert skilled in the art and refers to oligomeric compounds, primarily to oligonucleotides, but also to modified oligonucleotides that are able to prime DNA synthesis by a template-dependent DNA polymerase, i.e. the 3'-end of the primer provides a free 3'-OH group to which further nucleotides may be attached by a template-dependent DNA polymerase establishing 3'- to 5'-phosphodiester linkage whereby deoxynucleoside triphosphates are used and whereby pyrophosphate is released.

A "probe" also denotes a natural or modified oligonucleotide. As known in the art, a probe serves the purpose to detect an analyte or amplificate. In the case of the process described above, probes can be used to detect the amplificates of the target nucleic acids. For this purpose, probes typically carry labels.

"Labels", often referred to as "reporter groups", are generally groups that make a nucleic acid, in particular oligonucleotides or modified oligonucleotides, as well as any nucleic acids bound thereto distinguishable from the remainder of the sample (nucleic acids having attached a label can also be termed labeled nucleic acid binding compounds, labeled probes or just probes). Labels are in some embodiments fluorescent labels, which may be fluorescent dyes such as a fluorescein dye, a rhodamine dye, a cyanine dye, and a coumarin dye. Useful fluorescent dyes include FAM, HEX, JA270, CAL635, Coumarin343, Quasar705, Cyan500, CY5.5, LC-Red 640, LC-Red 705.

Any primer and/or probe may be chemically modified, i.e. the primer and/or the probe comprise a modified nucleotide or a non-nucleotide compound. The probe or the primer is then a modified oligonucleotide.

A method of nucleic acid amplification is the Polymerase Chain Reaction (PCR) which is well known to the skilled person, and disclosed, among other references, in U.S. Pat. No. 4,683,202, Other amplification reactions comprise, among others, the Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification.

Automated systems for PCR-based analysis often make use of real-time detection of product amplification during the PCR process in the same reaction vessel. Key to such methods is the use of modified oligonucleotides carrying reporter groups or labels, as described above.

The internal control nucleic acid described herein and comprising the sequence of SEQ ID NO 4 preferably exhibits the following properties relating to its sequence:

a melting temperature from 55° C. to 90° C., more preferably from 65° C. to 85° C., more preferably from 70° C. to 80° C., most preferably about 75° C.

a length of up to 500 bases or base pairs, more preferably from 50 to 300 bases or base pairs, more preferably from 100 to 200 bases or base pairs, most preferably about 180 bases or base pairs a GC content from 30% to 70%, more preferably from 40% to 60%, most preferably about 50%.

In some embodiments, the internal control nucleic acid consists of SEQ ID NO 4 or its complement. As used herein, a "sequence" is the primary structure of a nucleic acid, i.e. the specific arrangement of the single nucleobases of which the respective nucleic acids consists. It has to be understood that the term "sequence" does not denote a specific type of nucleic acid such as RNA or DNA, but applies to both as well as to other types of nucleic acids such as PNA or others. Where nucleobases correspond to each other, particularly in the case of uracil (present in RNA) and thymine (present in DNA), these bases can be considered equivalent between RNA and DNA sequences, as well-known in the pertinent art.

Clinically relevant nucleic acids are often DNA which can be derived from DNA viruses like Hepatitis B Virus (HBV), Cytomegalovirus (CMV) and others, or bacteria like *Chlamydia trachomatis* (CT), *Neisseria gonorrhoeae* (NG) and others. In such cases, it can be advantageous to use an internal control nucleic acid consisting of DNA, in order to reflect the target nucleic acids properties.

Therefore, in some embodiments, said internal control nucleic acid is DNA.

On the other hand, numerous nucleic acids relevant for clinical diagnostics are ribonucleic acids, like the nucleic acids from RNA viruses such as Human Immunodeficiency Virus (HIV), Hepatitis C Virus (HCV), the West Nile Virus (WNV), Human Papilloma Virus (HPV), Japanese Encephalitis Virus (JEV), St. Louis Encephalitis Virus (SLEV) and others. The process described herein can be readily applied to such nucleic acids. In this case, it can be advantageous to use an internal control nucleic acid consisting of RNA, in order to reflect the target nucleic acids properties. If both RNA and DNA are to be analyzed in the process described supra, it is the internal control nucleic acid may advantageously be RNA, as the internal control nucleic acid should ideally mimic the most sensitive target of an assay involving multiple targets, and RNA targets usually have to be more closely controlled.

Thus, in some embodiments the internal control nucleic acid described herein is RNA.

Since RNA is more prone to degradation than DNA due to influences such as alkaline pH, ribonucleases etc., internal control nucleic acids made of RNA are preferably provided as armored particles. Armored particles such as especially armored RNA are described in EP 910643. In brief, the RNA, which can be produced chemically or, preferably, heterologously by bacteria such as *E. coli*, is at least partially encapsulated in a viral coat protein. The latter confers resistance of the RNA towards external influences, in particular ribonucleases. It must be understood that internal control DNA can also be provided as a phage-packaged and thus protected particle. Both encapsulated RNA and DNA are useful as internal control nucleic acids in the context described herein. In some embodiments, RNA control nucleic acids are armored with the MS2 coat protein in *E. coli*. In a further embodiment, DNA control nucleic acids are armored using lambda phage GT11.

Typically, in amplification-based nucleic acid diagnostics, RNA templates are transcribed into DNA prior to amplification and detection.

Hence, in some embodiments of the process described herein, said amplification reagents comprise a polymerase with reverse transcriptase activity, the process further comprising between step e. and step f. the step of incubating in said reaction vessels said purified nucleic acids with said one or more amplification reagents for a period of time and under conditions suitable for transcription of RNA by said polymerase with reverse transcriptase activity to occur.

A "polymerase with reverse transcriptase activity" is a nucleic acid polymerase capable of synthesizing DNA based on an RNA template. It is also capable of the formation of a double-stranded DNA once the RNA has been reverse transcribed into a single strand cDNA. In some embodiments, the polymerase with reverse transcriptase activity is thermostable.

In the amplification of an RNA molecule by a DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a DNA polymerase provides the starting material for amplification.

Thermostable DNA polymerases can be used in a coupled, one-enzyme reverse transcription/amplification reaction. The term "homogeneous", in this context, refers to a two-step single addition reaction for reverse transcription and amplification of an RNA target. By homogeneous it is meant that following the reverse transcription (RT) step, there is no need to open the reaction vessel or otherwise adjust reaction components prior to the amplification step. In a non-homogeneous RT/PCR reaction, following reverse transcription and prior to amplification one or more of the reaction components such as the amplification reagents may be adjusted, added, or diluted, for which the reaction vessel has to be opened, or at least its contents have to be manipulated.

Reverse transcription is an important step in an RT/PCR. It is, for example, known in the art that RNA templates show a tendency towards the formation of secondary structures that may hamper primer binding and/or elongation of the cDNA strand by the respective reverse transcriptase. Thus, relatively high temperatures for an RT reaction are advantageous with respect to efficiency of the transcription. On the other hand, raising the incubation temperature also implies higher specificity, i.e. the RT primers will not anneal to sequences that exhibit mismatches to the expected sequence or sequences. Particularly in the case of multiple different target RNAs, it can be desirable to also transcribe and subsequently amplify and detect sequences with single mismatches, for example, in the case of the possible presence of unknown or rare substrains or subspecies of organisms in the fluid sample.

In order to benefit from both advantages described above, i.e. the reduction of secondary structures and the reverse transcription of templates with mismatches, in some embodiments the RT incubation is carried out at more than one distinct temperature.

Therefore, in some embodiments, said incubation of the polymerase with reverse transcriptase activity is carried out at different temperatures from 30° C. to 75° C., from 45° C. to 70° C., or from 55° C. to 65° C.

As a further important aspect of reverse transcription, long RT steps can damage the DNA templates that may be present in the fluid sample. If the fluid sample contains both RNA and DNA species, it can thus be favorable to keep the duration of the RT steps as short as possible, but at the same time ensuring the synthesis of sufficient amounts of cDNA for the subsequent amplification and optional detection of amplificates.

Thus, in some embodiments the period of time for incubation of the polymerase with reverse transcriptase activity is up to 30 minutes, 20 minutes, 15 minutes, 12.5 minutes, 10 minutes, 5 minutes, or 1 minute.

In a further embodiment, the polymerase with reverse transcriptase activity and comprising a mutation is selected from the group consisting of a) a CS5 DNA polymerase
b) a CS6 DNA polymerase
c) a *Thermotoga maritima* DNA polymerase
d) a *Thermus aquaticus* DNA polymerase
e) a *Thermus thermophilus* DNA polymerase
f) a *Thermus flavus* DNA polymerase
g) a *Thermus filiformis* DNA polymerase
h) a *Thermus* sp. sps17 DNA polymerase
i) a *Thermus* sp. Z05 DNA polymerase
j) a *Thermotoga neapolitana* DNA polymerase
k) a *Termosipho africanus* DNA polymerase
l) a *Thermus caldophilus* DNA polymerase Particularly suitable for these requirements are enzymes carrying a mutation in the polymerase domain that enhances their reverse transcription efficiency in terms of a faster extension rate.

Therefore, in some embodiments the polymerase with reverse transcriptase activity is a polymerase comprising a mutation conferring an improved nucleic acid extension rate and/or an improved reverse transcriptase activity relative to the respective wildtype polymerase.

In some embodiments, the polymerase with reverse transcriptase activity is a polymerase comprising a mutation conferring an improved reverse transcriptase activity relative to the respective wildtype polymerase.

Polymerases carrying point mutations that render them particularly useful in the context of the invention are disclosed in WO 2008/046612. In particular, in some embodiments polymerases to be used in the context of the present invention are mutated DNA polymerases comprising at least the following motif in the polymerase domain:

T-G-R-L-S-S-$X_{b7}$-$X_{b8}$-P-N-L-Q-N (SEQ ID NO 15); wherein $X_{b7}$ is an amino acid selected from S or T and wherein $X_{b8}$ is an amino acid selected from G, T, R, K, or L, wherein the polymerase comprises 3'-5' exonuclease activity and has an improved nucleic acid extension rate and/or an improved reverse transcription efficiency relative to the wildtype DNA polymerase, wherein in said wildtype DNA polymerase $X_{b8}$ is an amino acid selected from D, E or N.

Particularly useful are mutants of the thermostable DNA polymerase from *Thermus* species Z05 (described e.g. in U.S. Pat. No. 5,455,170), said variations comprising mutations in the polymerase domain as compared with the respective wildtype enzyme Z05. Especially useful is a mutant Z05 DNA polymerase wherein the amino acid at position 580 is selected from the group consisting of G, T, R, K and L.

For reverse transcription using a thermostable polymerase, Mn2+ may be used as the divalent cation and is typically included as a salt, for example, manganese chloride (MnCl2), manganese acetate (Mn(OAc)2), or manganese sulfate (MnSO4). If MnCl2 is included in a reaction containing 50 mM Tricine buffer, for example, the MnCl2 is generally present at a concentration of 0.5-7.0 mM; 0.8-1.4 mM may be present when 200 mM of each dGTP, dATP, dUTP, and, dCTP are utilized; and 2.5-3.5 mM MnCl2 may be present. Further, in some embodiments Mg2+ is used as a divalent cation for reverse transcription.

Since it is included in some embodiments to reverse-transcribe RNA target nucleic acids into cDNA while preserving the DNA target nucleic acids so both cDNA and DNA can be used for subsequent amplification, the internally controlled process described herein is particularly useful for the simultaneous amplification and detection of target nucleic acids derived from both organisms having an RNA or organisms having a DNA genome. This advantage considerably increases the spectrum of different organisms, especially pathogens, that can be analyzed under identical physical conditions.

Therefore, in some embodiments the first and second target nucleic acids comprise RNA and DNA.

The target of the amplification step can be an RNA/DNA hybrid molecule. The target can be a single-stranded or double-stranded nucleic acid. Although the most widely used PCR procedure uses a double-stranded target, this is not a necessity. After the first amplification cycle of a single-stranded DNA target, the reaction mixture contains a double-stranded DNA molecule consisting of the single-stranded target and a newly synthesized complementary strand. Similarly, following the first amplification cycle of an RNA/cDNA target, the reaction mixture contains a double-stranded cDNA molecule. At this point, successive cycles of amplification proceed as described above.

In some embodiments, the amplified target nucleic acids and the amplified internal control nucleic acid are detected during or after the amplification reaction in order to evaluate the result of the analysis.

It can be favorable to monitor the amplification reaction in real time, i.e. to detect the amplified target nucleic acids and the amplified internal control nucleic acid during the amplification itself.

Therefore, in some embodiments, the probes, and in particular the probe with SEQ ID NO 1, are labeled with a donor fluorescent moiety and a corresponding acceptor fluorescent moiety.

The methods set out above are preferably based on Fluorescence Resonance Energy Transfer (FRET) between a donor fluorescent moiety and an acceptor fluorescent moiety. A representative donor fluorescent moiety is fluorescein, and representative corresponding acceptor fluorescent moieties include LC-Red 640, LC-Red 705, Cy5, and Cy5.5. Typically, detection includes exciting the sample at a wavelength absorbed by the donor fluorescent moiety and visualizing and/or measuring the wavelength emitted by the corresponding acceptor fluorescent moiety. In the process according to the invention, detection is preferably followed by quantitating the FRET. Preferably, detection is performed after each cycling step. Most preferably, detection is performed in real time. By using commercially available real-time PCR instrumentation (e.g., LightCycler™ or TaqMan®), PCR amplification and detection of the amplification product can be combined in a single closed cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The LightCycler™ instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the thermal chamber.

TaqMan® technology utilizes a single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. Typical fluorescent dyes used in this format are for example, among others, FAM, HEX, CY5, JA270, Cyan and CY5.5. During the annealing step of the PCR reaction, the labeled hybridization probe binds to the target nucleic acid (i.e., the amplification product) and is degraded by the 5' to 3' exonuclease activity of the Taq or another suitable polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected.

In both detection formats described above, the intensity of the emitted signal can be correlated with the number of original target nucleic acid molecules.

As an alternative to FRET, an amplification product can be detected using a double-stranded DNA binding dye such as a fluorescent DNA binding dye (e.g., SYBRGREEN I® or SYBRGOLD® (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g. a hairpin). As a result of secondary structure formation within the probe, both fluorescent moieties are in spatial proximity when the probe is in solution. After hybridization to the amplification products, the secondary structure of the probe is disrupted and the fluorescent moieties become separated from one another such that after excitation with light of a suitable wavelength, the emission of the first fluorescent moiety can be detected.

Thus, in some embodiment the process described herein uses FRET, wherein the probes comprise a nucleic acid sequence that permits secondary structure formation, wherein said secondary structure formation results in spatial proximity between said first and second fluorescent moiety.

Efficient FRET can only take place when the fluorescent moieties are in direct local proximity and when the emission spectrum of the donor fluorescent moiety overlaps with the absorption spectrum of the acceptor fluorescent moiety.

Thus, in some embodiments, said donor and acceptor fluorescent moieties are within no more than 5 nucleotides of each other on said probe.

In a further embodiment, said acceptor fluorescent moiety is a quencher.

It is further advantageous to carefully select the length of the amplicon that is yielded as a result of the process described above. Generally, relatively short amplicons increase the efficiency of the amplification reaction. Thus, a preferred aspect of the invention is the process described above, wherein the amplified fragments comprise up to 450 bases, preferably up to 300 bases, further preferably up to 200 bases, and further preferably up to 150 bases.

The internal control nucleic acid described herein can serve as a "quantitative standard nucleic acid" which is apt to be and used as a reference in order to quantify, i.e. to determine the quantity of the target nucleic acids. For this purpose, one or more quantitative standard nucleic acids undergo all possible sample preparation steps along with the target nucleic acids. Moreover, a quantitative standard nucleic acid is processed throughout the method within the same reaction mixture. It must generate, directly or indirectly, a detectable signal both in the presence or absence of the target nucleic acid. For this purpose, the concentration of the quantitative standard nucleic acid has to be carefully optimized in each test in order not to interfere with sensitivity but in order to generate a detectable signal also at very high target concentrations. In terms of the limit of detection (LOD, see below) of the respective assay, the concentration range for the "quantitative standard nucleic acid" is in some embodiments 20-5000×LOD, in further embodiments 20-1000×LOD, and in yet further embodiments 20-5000×LOD. The final concentration of the quantitative standard nucleic acid in the reaction mixture is dependent on the quantitative measuring range accomplished.

"Limit of detection" or "LOD" means the lowest detectable amount or concentration of a nucleic acid in a sample. A low "LOD" corresponds to high sensitivity and vice versa. The "LOD" is usually expressed either by means of the unit "cp/ml", particularly if the nucleic acid is a viral nucleic acid, or as IU/ml. "Cp/ml" means "copies per milliliter" wherein a "copy" is copy of the respective nucleic acid. IU/ml stands for "International units/ml", referring to the WHO standard.

A widely used method for calculating an LOD is "Probit Analysis", which is a method of analyzing the relationship between a stimulus (dose) and the quantal (all or nothing) response. In a typical quantal response experiment, groups of animals are given different doses of a drug. The percent dying at each dose level is recorded. These data may then be analyzed using Probit Analysis. The Probit Model assumes that the percent response is related to the log dose as the cumulative normal distribution. That is, the log doses may be used as variables to read the percent dying from the cumulative normal. Using the normal distribution, rather than other probability distributions, influences the predicted response rate at the high and low ends of possible doses, but has little influence near the middle.

The Probit Analysis can be applied at distinct "hitrates". As known in the art, a "hitrate" is commonly expressed in percent [%] and indicates the percentage of positive results at a specific concentration of an analyte. Thus for example, an LOD can be determined at 95% hitrate, which means that the LOD is calculated for a setting in which 95% of the valid results are positive.

An example of how to perform calculation of quantitative results in the TaqMan format based on an internal control nucleic acid serving as a quantitative standard nucleic acid is described in the following: A titer is calculated from input data of instrument-corrected fluorescence values from an entire PCR run. A set of samples containing a target nucleic acid and an internal control nucleic acid serving as a quantitative standard nucleic acid undergo PCR on a thermocycler using a specified temperature profile. At selected temperatures and times during the PCR profile samples are illuminated by filtered light and the filtered fluorescence data are collected for each sample for the target nucleic acid and the internal control nucleic acid. After a PCR run is complete, the fluorescence readings are processed to yield one set of dye concentration data for the internal control nucleic acid and one set of dye concentration data for the target nucleic acid. Each set of dye concentration data is processed in the same manner. After several plausibility checks, the elbow values (CT) are calculated for the internal control nucleic acid and the target nucleic acid. The elbow value is defined as the point where the fluorescence of the target nucleic acid or the internal control nucleic acid crosses a predefined threshold (fluorescence concentration). Titer determination is based on the assumptions that the target nucleic acid and the internal control nucleic acid are amplified with the same efficiency and that at the calculated elbow value equal amounts of amplicon copies of target nucleic acid and internal control nucleic acid are amplified and detected. Therefore, the (CTQS−CTtarget) is linear to log (target conc/QS conc). In this context, QS denotes the internal control nucleic acid serving as a quantitative standard nucleic acid. The titer T can then be calculated for instance by using a polynomial calibration formula as in the following equation:

$$T'=10(a(CTQS-CT\text{target})2+b(CTQS-CT\text{target})+c)$$

The polynomial constants and the concentration of the quantitative standard nucleic acid are known, therefore the only variable in the equation is the difference (CTQS−CTtarget).

Further, the internal control nucleic acid can in some embodiments serve as a "qualitative internal control nucleic acid". A "qualitative internal control nucleic acid" is particularly useful for confirming the validity of the test result of a qualitative detection assay: Even in the case of a negative result, the qualitative internal control must be detected, otherwise the test itself is considered to be inoperative. However, in a qualitative setup, it does not necessarily have to be detected in case of a positive result. As a consequence, its concentration must be relatively low. It has to be carefully adapted to the respective assay and its sensitivity. In some embodiments, the concentration for the qualitative internal nucleic acid is in a range of 1 copy per reaction to 1000 copies per reaction. In relation to the respective assay's limit of detection (LOD), its concentration is in some embodiments between the LOD of an assay and the 25fold value of the LOD, in further embodiments between the LOD and 10×LOD. In yet further embodiments, it is between 2× and 10×LOD. In other embodiments, it is between 5× and 10×LOD, or it is 5× or 10×LOD.

In some embodiments, it can be advantageous to add different internal control nucleic acids to a fluid samples, but to use only one of them—at least the one comprising the sequence of SEQ ID NO 4—for amplification and detection by adding only the primers with SEQ ID NO 2 and SEQ ID NO 3 and the probe with SEQ ID NO 1.

In some embodiments of the process described herein, all steps are automated. "Automated" means that the steps of a process are suitable to be carried out with an apparatus or machine capable of operating with little or no external control or influence by an individual. Only the preparation steps for the method may have to be done by hand, for instance, storage containers have to be filled and put into place, the choice of samples has to be performed by a human being and further steps known to the expert in the field, such as the operation of a controlling computer. The apparatus or machine may automatically add liquids, mix the samples or carry out incubation steps at specific temperatures. Typically, such a machine or apparatus is a robot controlled by a computer which carries out a program in which the single steps and commands are specified.

DESCRIPTION OF THE FIGURES

FIG. 1:

Schematic depiction of the sample preparation workflow as used in an embodiment of the invention.

Arrows pointing down denote addition of a component or reagent to each respective well of the deepwell plate mentioned above, arrows pointing up their respective removal. These actions were performed manually in steps 2, 3, 4, 21 and 22, by the process head of the apparatus in steps 10, 14, 16, 18, and 24, and by the reagent head of the apparatus in steps 5, 6, 7, 11, 15 and 19.

It has to be understood that the volumes used can be adjusted flexibly within the spirit of the invention, preferably at least about up to 30% of the disclosed values. In particular, in the case of step 2, the sample volume is preferably variable in order to take into account the different types of fluid samples which may require more or less starting material for obtaining proper results, as known by the artisan. Preferably, the range is from about 100 ul to about 850 ul. More preferably, it is about 100 ul, about 500 ul or about 850 ul. Preferably, the volume in the respective vessels is adjusted to an identical total volume with the diluent in step 3. Preferably, as in the scheme shown in FIG. 1, the total volume adds up to about 850 ul.

EXAMPLE

This example describes the performance comparison of two different oligonucleotide sets targeting SEQ ID NO 4 (set 2 containing SEQ ID NOs 2, 3 and 5 (in MMx R2-SEQ ID NO 5), and set 3 containing SEQ ID NOs 2, 3 and 1 (in MMx R2-SEQ ID NO 1), and a reference set 1 containing SEQ ID NOs 6, 7 and 8 (in MMx R2-Reference/SEQ ID NO 6) targeting SEQ ID NO 9.

In brief, in the depicted embodiment, realtime PCR is carried out on an RNA virus (HCV) using an internal control nucleic acid comprising the sequences of both SEQ ID NO 4 and SEQ ID NO 9. All samples were processed and analyzed within the same experiment, i.e. on the same multiwell plate.

The following samples were prepared and subsequently analyzed:

| Reagent | Manufacturer: |
|---|---|
| HCV Secondary Standard, 18000 IU/ml | Roche |
| Plasmid comprising SEQ ID NOs 4 & 9 3E11parts/mL | Roche |

Suitable other types of standards or targets are known and available to the skilled artisan.

The instruments listed in the following table were used according to the instructions of the respective manufacturer:

| Instrument | Manufacturer |
|---|---|
| cobas ® 6800/8800 process cell | Roche Diagnostics AG (Rotkreuz, CH) |
| cobas ® 6800/8800 analytical cycler | Roche Diagnostics AG (Rotkreuz, CH) |

For sample preparation the following reagents were used as diluents:

| Reagent | Manufacturer: |
|---|---|
| BULK MP SPECIMEN DILUENT PMC (MPSD) - IC/IQS Storage Buffer | Roche |
| K3 EDTA Plasma, PCR neg. | Roche |

The following dilutions were prepared in advance and stored overnight (plasma dilutions at −60 to −90° C., BULK MP SPECIMEN DILUENT PMC dilutions at 2-8° C.):

| Target | Concentration | Matrix |
|---|---|---|
| HCV | 10 IU/ml | K3 EDTA plasma |
| SEQ ID NO 4 | 6.0E+04 parts/ml | BULK MP SPECIMEN DILUENT PMC (MPSD) |

Each respective sample (500 ul) and each respective specimen diluent (350 ul) were pipetted manually into a deepwell plate. To each well containing an HCV sample, 50 ul of the quantitative control nucleic acid mentioned above (3000 particles/sample) were manually added.

The respective control nucleic acid was stored in the following buffer:

| IC/IQS - Storage Buffer, MPSD | Conc. or pH |
|---|---|
| Tris (mM) | 10 |
| EDTA (mM) | 0.1 |
| Sodium Azide (w/v, %) | 0.05 |

-continued

| IC/IQS - Storage Buffer, MPSD | Conc. or pH |
|---|---|
| Poly rA RNA (mg/l) | 20 |
| pH | 8 |

Sample preparation was performed on a Cobas®6800/8800 process cell (Roche Diagnostics AG, Rotkreuz, C H), following the workflow according to the scheme depicted in FIG. 1 and using the following reagents:

| Protease reagent | Conc. or pH |
|---|---|
| Tris (mM) | 10 |
| EDTA (mM) | 1 |
| Calcium Chloride (mM) | 5 |
| Calcium Acetate (mM) | 5 |
| Esperase (mg/ml) | 80 |
| Glycerin (w/v, %) | 50 |
| pH | 5.5 |

| MGP Reagent | Conc. or pH |
|---|---|
| MPG Powder (mg/ml) | 60 |
| Tris (mM) | 30 |
| Methylparaben (w/v, %) | 0.1 |
| Sodium Azide (w/v, %) | 0.095 |
| pH | 8.5 |

| Lysis Reagent | Conc. or pH |
|---|---|
| Guanidine Thiocyanate (M) | 4 |
| Sodium Citrate (mM) | 50 |
| Polydocanol (w/v, %) | 5 |
| Dithiotreitol (w/v, %) | 2 |
| pH | 5.8 |

| Wash buffer | Conc. or pH |
|---|---|
| Sodium Citrate (mM) | 7.5 |
| Methylparaben (w/v, %) | 0.1 |
| pH | 4.1 |

| Elution buffer | Conc. or pH |
|---|---|
| Tris (mM) | 30 |
| Methylparaben (w/v, %) | 0.09 |
| pH | 9.1 |

During the final sample preparation step (eluate cool down) the working Master Mixes (MMx), containing amplification reagents MMx R1 and MMx R2, were added manually to each well of a microwell plate. The eluates (containing the isolated nucleic acids) were then transferred by the instrument from the p-plate to the micro-well plate and mixed with the MMx. The microwell plates were then sealed automatically and transferred manually into the stand-alone analytical cycler for amplification and detection.

The following master mixes (each consisting of the two reagents R1 and R2) were used:

For MMx R2-Reference/SEQ ID NO 6:

| R1 Reagent | Concentration/50 µl-PCR [µM] |
|---|---|
| Water (PCR grade) | |
| $Mn(Ac)_2$ * $4H_2O$ (pH 6.1 adjusted with Acetic Acid) | 3300 |
| NaN3/Ri, buffered with 10 mM Tris at pH 7 [%] | 0.018 |

| R2 Reagent | Concentration/50 µl-PCR [µM] |
|---|---|
| DMSO [%] | 5.400% |
| NaN3/Ri, buffered with 10 mM Tris at pH 7 [%] | 0.027% |
| Potassium acetate pH 7.0 | 120'000 |
| Glycerol [%] | 3.000% |
| Tween 20 (%) | 0.015% |
| Tricine pH 8.0 | 60'000 |
| NTQ21-46A - Aptamer | 0.2222 |
| UNG (U/uL) | 0.2 |
| dGTP | 400 |
| dATP | 400 |
| dCTP | 4000 |
| dUTP | 800 |
| 10 mM Tris buffer for primer | 1.800 |
| SEQ ID NO 10 (HCV primer) | 0.100 |
| SEQ ID NO 11 (HCV primer) | 0.100 |
| SEQ ID NO 12 (HCV primer) | 0.100 |
| SEQ ID NO 7 (IC primer) | 0.300 |
| SEQ ID NO 8 (IC primer) | 0.300 |
| probe storage buffer FAM/HEX | 0.550 |
| SEQ ID NO 13 (HCV probe) | 0.100 |
| SEQ ID NO 14 (HCV probe) | 0.100 |
| SEQ ID NO 6 (IC probe) | 0.100 |
| Z05-D Polymerase (U/uL) | 40 (U/reaction) |
| Water | |

For in MMx R2-SEQ ID NO 5:

| R1 Reagent | Concentration/50 µl-PCR [µM] |
|---|---|
| Water (PCR grade) | |
| Mn(Ac)2 * 4H2O (pH 6.1 adjusted with Acetic Acid) | 3300 |
| NaN3/Ri, buffered with 10 mM Tris at pH 7 [%] | 0.018 |

| R2 Reagent | Concentration/50 µl-PCR [µM] |
|---|---|
| DMSO [%] | 5.400% |
| NaN3/Ri, buffered with 10 mM Tris at pH 7 [%] | 0.027% |
| Potassium acetate pH 7.0 | 120'000 |
| Glycerol [%] | 3.000% |
| Tween 20 (%) | 0.015% |
| Tricine pH 8.0 | 60'000 |
| NTQ21-46A - Aptamer | 0.2222 |
| UNG (U/uL) | 0.2 |
| dGTP | 400 |
| dATP | 400 |
| dCTP | 4000 |
| dUTP | 800 |
| 10 mM Tris buffer for primer | 1.800 |
| SEQ ID NO 10 (HCV primer) | 0.100 |
| SEQ ID NO 11 (HCV primer) | 0.100 |
| SEQ ID NO 12 (HCV primer) | 0.100 |
| SEQ ID NO 2 (IC primer) | 0.300 |
| SEQ ID NO 3 (IC primer) | 0.300 |

-continued

| R2 Reagent | Concentration/50 μl-PCR [μM] |
|---|---|
| probe storage buffer FAM/HEX | 0.550 |
| SEQ ID NO 13 (HCV probe) | 0.100 |
| SEQ ID NO 14 (HCV probe) | 0.100 |
| SEQ ID NO 5 (IC Probe) | 0.100 |
| Z05-D Polymerase (U/uL) | 40 (U/reaction) |
| Water | |

For in MMx R2-SEQ ID NO 1:

| R1 Reagent | Concentration/50 μl-PCR [μM] |
|---|---|
| Water (PCR grade) | |
| Mn(Ac)2 * 4H2O (pH 6.1 adjusted with Acetic Acid) | 3300 |
| NaN3/Ri, buffered with 10 mM Tris at pH 7 [%] | 0.018 |

| R2 Reagent | Concentration/50 μl-PCR [μM] |
|---|---|
| DMSO [%] | 5.400% |
| NaN3/Ri, buffered with 10 mM Tris at pH 7 [%] | 0.027% |
| Potassium acetate pH 7.0 | 120'000 |
| Glycerol [%] | 3.000% |
| Tween 20 (%) | 0.015% |
| Tricine pH 8.0 | 60'000 |
| NTQ21-46A - Aptamer | 0.2222 |
| UNG (U/uL) | 0.2 |
| dGTP | 400 |
| dATP | 400 |
| dCTP | 4000 |
| dUTP | 800 |
| 10 mM Tris buffer for primer | 1.800 |
| SEQ ID NO 10 (HCV primer) | 0.100 |
| SEQ ID NO 11 (HCV primer) | 0.100 |
| SEQ ID NO 12 (HCV primer) | 0.100 |
| SEQ ID NO 2 (IC primer) | 0.300 |
| SEQ ID NO 3 (IC primer) | 0.300 |
| probe storage buffer FAM/HEX | 0.550 |
| SEQ ID NO 13 (HCV probe) | 0.100 |
| SEQ ID NO 14 (HCV probe) | 0.100 |
| SEQ ID NO 1 (IC Probe) | 0.100 |
| Z05-D Polymerase (U/uL) | 40 (U/reaction) |
| Water | |

For amplification and detection, the microwell plate was sealed with an automated plate sealer in the Cobas® 6800/8800 process cell (see above), and the plate was manually transferred to the Cobas® 6800/8800 analytical cycler (see above).

The amplification and detection (Real Time PCR) was carried out simultaneously and under identical conditions for the three Master Mixes using the generic PCR profile shown in Table 1. In total, seven Amplification-Detection-Plates were run to obtain the required replicates.

TABLE 1

| Thermocycling profile | | | | | | |
|---|---|---|---|---|---|---|
| | | Target [° C.] | Acquisition Mode | Plateau [hh:mm:ss] | Measure [hh:mm:ss] | Ramp Rate [° C./s] |
| Pre-PCR | UNG-Step | 50 | none | 00:02:00 | 00:00:00 | 2.2 |
| | UNG/Template Denaturation | 94 | none | 00:00:05 | 00:00:00 | 4.4 |
| | RT-Step | 55 | none | 00:02:00 | 00:00:00 | 2.2 |
| | | 60 | none | 00:06:00 | 00:00:00 | 4.4 |
| | | 65 | none | 00:04:00 | 00:00:00 | 4.4 |
| 1st Measurement | | 95 | none | 00:00:05 | 00:00:00 | 4.4 |
| | | 55 | single | 00:00:30 | 00:00:08 | 2.2 |
| 2nd Measurement | | 91 | none | 00:00:05 | 00:00:00 | 4.4 |
| | | 58 | single | 00:00:25 | 00:00:08 | 2.2 |
| Cooling | | 40 | none | 00:02:00 | 00:00:00 | 2.2 |

TABLE 2

| Cycles Overview | |
|---|---|
| Name | Cycles |
| Pre-PCR | 1 |
| 1st Measurement | 5 |
| 2nd Measurement | 45 |
| Cooling | 1 |

TABLE 3

| Integration times | |
|---|---|
| Filter Combination | Integration Time (sec) |
| 435-470 | 0.30 |
| 495-525 | 0.50 |
| 540-580 | 0.50 |
| 610-645 | 0.20 |
| 680-700 | 1.00 |

The Pre-PCR program comprised initial denaturing and incubation at 55, 60 and 65° C. for reverse transcription of RNA templates. Incubating at three temperatures combined the advantageous effects that at lower temperatures slightly mismatched target sequences (such as genetic variants of an organism) are also transcribed, while at higher temperatures the formation of RNA secondary structures is suppressed, thus leading to a more efficient transcription.

PCR cycling was divided into two measurements, wherein both measurements applied a one-step setup (combining annealing and extension). The first 5 cycles at 55° C. allowed for an increased inclusivity by pre-amplifying slightly mismatched target sequences, whereas the 45 cycles of the second measurement provided for an increased specificity by using an annealing/extension temperature of 58° C.

Using this profile on all samples comprised on the microwell plate mentioned above, amplification and detection was achieved in all samples. This shows that the sample preparation prior to amplification was also successfully carried out.

The results show that the controls were also successfully amplified in all cases. The quantitation of the HCV target in the quantitative setup was calculated by comparison with the respective internal control nucleic acid serving as a quantitative standard.

Data Analysis

The raw data files of the Analytical Cycler (xml file) were analyzed using the PARTS software. The current Cobas® 6800/8800 HCV analysis template was used for data calculation, as well as positive/negative calling for the three master mixes in channel 4/JA270 (HCV signal) and channel 5/Cy5.5 (quantitative control signal). For HCV target and quantitative control the hit rates, CT, RFI and F-values were calculated with the current Cobas® 6800/8800 HCV analysis template Results The hit rates, CT-, RFI- and FValues for the three Master Mixes are listed in Tables 4 and 5. The used analysis template was not optimized for each of the oligonucleotide sets.

TABLE 4

HCV Target CT values and RFI values with 500 uL sample process input volume for EDTA Plasma

| Sample Comment | Hit rate | Hit rate (%) | | CT value | RFI | FValue |
|---|---|---|---|---|---|---|
| 10 IU/mL HCV | 85 of | 85.00% | average | 40.03 | 13.73 | 1172262 |
| MMx R2-Ref./ | 100 | | STDEV | 0.85 | 2.83 | 1122635 |
| SEQ ID NO 6 | | | CV | 2.13% | 20.61% | 95.77% |
| 10 IU/mL HCV | 90 of | 92.78% | average | 40.56 | 9.10 | 477216 |
| MMx R2- | 97 | | STDEV | 1.16 | 2.19 | 626006 |
| SEQ ID NO 5 | | | CV | 2.86% | 24.09% | 131.18% |
| 10 IU/mL HCV | 93 of | 93.00% | average | 40.21 | 10.01 | 641844 |
| MMx R2- | 100 | | STDEV | 0.88 | 2.16 | 749487 |
| SEQ ID NO 1 | | | CV | 2.19% | 21.56% | 116.77% |

TABLE 5

Internal control CT values and RFI values with 500 uL sample process input volume for EDTA Plasma

| Sample Comment | Hit rate | Hit rate (%) | | CT value | RFI | FValue |
|---|---|---|---|---|---|---|
| MMx R2- | 100 of | 100.00% | average | 33.30 | 46.61 | 179536 |
| Reference/ | 100 | | STDEV | 0.67 | 8.57 | 69381 |
| SEQ ID NO 6 | | | CV | 2.02% | 18.40% | 38.64% |
| 10 IU/mL HCV | 97 of | 97.00% | average | 33.84 | 3.27 | 121976 |
| MMx R2- | 100 | | STDEV | 0.46 | 0.18 | 70998 |
| SEQ ID NO 5 | | | CV | 1.37% | 5.54% | 58.21% |
| 10 IU/mL HCV | 100 of | 100.00% | average | 33.64 | 11.42 | 188650 |
| MMx R2- | 100 | | STDEV | 0.31 | 0.86 | 145133 |
| SEQ ID NO 1 | | | CV | 0.92% | 7.53% | 76.93% |

Summary Probe Comparison:

The three internal control oligonucleotide sets, compared in a side-by-side study, showed no significant difference in hit rate. A trend towards a better RFI value combined with a lower base line with MMx R2-SEQ ID NO 1 (oligonucleotide set 3) was observed. This allows for an improved detection of the control nucleic acid comprising SEQ ID NO 4. By using the probe with SEQ ID NO 1 instead of SEQ ID NO 5, assays using an internal control nucleic acid comprising SEQ ID NO 4 thus become more reliable and robust.

What is claimed is:

1. A process for isolating and simultaneously amplifying a first and a second target nucleic acid that may be present in one or more fluid samples, said process comprising the automated steps of:

(a) adding an internal control nucleic acid comprising the sequence of SEQ ID NO 4 to each of said fluid samples (b) combining together a solid support material and said one or more fluid samples in one or more vessels for a period of time and under conditions sufficient to permit nucleic acids comprising the target nucleic acids, if present on said one or more fluid samples, and the internal control nucleic acid to be immobilized on the solid support material (c) isolating the solid support material from the other material present in the fluid samples in a separation station (d) purifying the nucleic acids in said separation station and washing the solid support material one or more times with a wash buffer (e) contacting the purified target nucleic acids and the purified internal control nucleic acid with amplification reagents comprising a distinct set of primers and a probe for each of said target nucleic acids and a set of primers comprising a first primer with a sequence consisting of SEQ ID NO 2 and a second primer with a sequence consisting of SEQ ID NO 3 and a probe with a sequence consisting of SEQ ID NO 1 and attached to a detectable label for said internal control nucleic acid in at least two reaction vessels, wherein a first reaction vessel comprises primers and a probe for said first target nucleic acid and at least a second reaction vessel comprises primers and a probe for said second target nucleic acid and wherein the primers and the probe for the first target nucleic acid are absent from the second reaction vessel and the primers and the probe for the second target nucleic acid are absent from the first reaction vessel (f) incubating in said reaction vessels said purified target nucleic acids and said purified internal control nucleic acid with said amplification reagents for a period of time and under conditions sufficient for an amplification reaction indicative of the presence or absence of said target nucleic acids to occur; and (g) detecting and measuring signals generated by the amplification products of said target nucleic acids and being proportional to the concentration of said target nucleic acids, and detecting and measuring a signal generated by said internal control nucleic acid, wherein the conditions for amplification and detection in steps (d) to (g) are identical for the first and the second reaction vessel and thus for the target nucleic acids and the internal control nucleic acid.

2. The process of claim 1, wherein the presence of an amplification production of said internal control nucleic acid is indicative of an amplification occurring in the reaction mixture even in the absence of amplification products for one or more of said target nucleic acids.

3. The process of claim 2, further comprising the following step:

(h) determining the quantity of one or more of said target nucleic acids.

4. The process of claim 1, wherein said amplification reagents comprise a polymerase with reverse transcriptase activity, said process further comprising between step (e) and step (f), the step of incubating in said reaction vessels said purified nucleic acids with said one or more amplification reagents for a period of time and under conditions suitable for transcription of RNA by said polymerase with reverse transcriptase activity to occur.

5. The process of claim 1, wherein said internal control nucleic acid is RNA or DNA.

6. The process of claim 1, wherein said internal control nucleic acid comprises an armored RNA or a phage-packaged DNA.

7. The process of claim 1, wherein the melting temperature of said internal control nucleic acid is from 50° C. to 90° C.

8. The process of claim 1, wherein the internal control nucleic acid has a length of up to 500 bases.

9. The process of claim 1, wherein the sequence of the internal control nucleic acid has a GC content of 30% to 70%.

10. The process of claim 1, wherein more than one internal control nucleic acid is added in step (a), but only one of said internal control nucleic acids is amplified in step (f).

11. The process of claim 2, wherein said amplification reagents comprise a polymerase with reverse transcriptase activity, said process further comprising between step (e) and step (f), the step of incubating in said reaction vessels said purified nucleic acids with said one or more amplification reagents for a period of time and under conditions suitable for transcription of RNA by said polymerase with reverse transcriptase activity to occur.

12. The process of claim 3, wherein said amplification reagents comprise a polymerase with reverse transcriptase activity, said process further comprising between step (e) and step (f), the step of incubating in said reaction vessels said purified nucleic acids with said one or more amplification reagents for a period of time and under conditions suitable for transcription of RNA by said polymerase with reverse transcriptase activity to occur.

* * * * *

SEQUENCE LISTING

```
<160> NUMBER OF SEQ ID NOS: 15

<210> SEQ ID NO 1
<211> LENGTH: 33
<212> TYPE: DNA
<213> ORGANISM: Artificial Sequence
<220> FEATURE:
<223> OTHER INFORMATION: IC Probe

<400> SEQUENCE: 1
```

```
tgcgcgtccc gttttgatac ttcgtaacgg tgc                                  33


<210> SEQ ID NO 2
<211> LENGTH: 25
<212> TYPE: DNA
<213> ORGANISM: Artificial Sequence
<220> FEATURE:
<223> OTHER INFORMATION: IC Primer

<400> SEQUENCE: 2

acaaccgcgc catacatgtc aagaa                                           25


<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3

gtcgggccgc ttatacagta ccaa                                            24


<210> SEQ ID NO 4
<211> LENGTH: 177
<212> TYPE: DNA
<213> ORGANISM: Artificial Sequence
<220> FEATURE:
<223> OTHER INFORMATION: Control nucleic acid

<400> SEQUENCE: 4

acaaccgcgc catacatgtc aagaatgaag tgggcgaacg ctagaaaact gacgccagca     60

attaagtgag tcggggcgtg gtgactccca cgtaaaaagc ccctaccccg caccgttacg    120

aagtatcaaa acgggacgcg cacgaaccga cgattggtac tgtataagcg gcccgac       177


<210> SEQ ID NO 5
<211> LENGTH: 32
<212> TYPE: DNA
<213> ORGANISM: Artificial Sequence
<220> FEATURE:
<223> OTHER INFORMATION: IC Probe

<400> SEQUENCE: 5

gccagcaatt aagtgagtcg gggcgtggtg ac                                   32


<210> SEQ ID NO 6
<211> LENGTH: 27
<212> TYPE: DNA
<213> ORGANISM: Artificial Sequence
<220> FEATURE:
<223> OTHER INFORMATION: IC probe

<400> SEQUENCE: 6

tctctcgcca tctcctaccg cattggc                                         27


<210> SEQ ID NO 7
<211> LENGTH: 25
<212> TYPE: DNA
<213> ORGANISM: Artificial Sequence
<220> FEATURE:
<223> OTHER INFORMATION: IC Primer

<400> SEQUENCE: 7

ttgatagcaa tcggctatcg actaa                                           25
```

<210> SEQ ID NO 8
<211> LENGTH: 28
<212> TYPE: DNA
<213> ORGANISM: Artificial Sequence
<220> FEATURE:
<223> OTHER INFORMATION: IC Primer

<400> SEQUENCE: 8
gcttcgatac tcagtcatct cggtataa 28

<210> SEQ ID NO 9
<211> LENGTH: 166
<212> TYPE: DNA
<213> ORGANISM: Artificial Sequence
<220> FEATURE:
<223> OTHER INFORMATION: Control nucleic acid

<400> SEQUENCE: 9
ttgatagcaa tcggctatcg actaatgact gtcctggcgg tctctcgcca tctcctaccg 60
cattggctca taggtaagct cgctgtcacc cagtacggag gtgccagtag attattagag 120
acagtcgcca atcgatcgtt ataccgagat gactgagtat cgaagc 166

<210> SEQ ID NO 10
<211> LENGTH: 26
<212> TYPE: DNA
<213> ORGANISM: Artificial Sequence
<220> FEATURE:
<223> OTHER INFORMATION: HCV Primer

<400> SEQUENCE: 10
gcagaaagcg tctagccatg gcgtta 26

<210> SEQ ID NO 11
<211> LENGTH: 25
<212> TYPE: DNA
<213> ORGANISM: Artificial Sequence
<220> FEATURE:
<223> OTHER INFORMATION: HCV Primer

<400> SEQUENCE: 11
gcaagcaccc tataggcagt accac 25

<210> SEQ ID NO 12
<211> LENGTH: 24
<212> TYPE: DNA
<213> ORGANISM: Artificial Sequence
<220> FEATURE:
<223> OTHER INFORMATION: HCV Primer

<400> SEQUENCE: 12
ctcgcaagca ccctatcagg cagt 24

<210> SEQ ID NO 13
<211> LENGTH: 33
<212> TYPE: DNA
<213> ORGANISM: Artificial Sequence
<220> FEATURE:
<223> OTHER INFORMATION: HCV Probe

<400> SEQUENCE: 13
ccgggagagc catagtggtc tgcggaaccg gtg 33

<210> SEQ ID NO 14
<211> LENGTH: 28

-continued

```
<212> TYPE: DNA
<213> ORGANISM: Artificial Sequence
<220> FEATURE:
<223> OTHER INFORMATION: HCV Probe

<400> SEQUENCE: 14

tctctcgccc atctcctacc gcattggc                                         28


<210> SEQ ID NO 15
<211> LENGTH: 13
<212> TYPE: PRT
<213> ORGANISM: Artificial Sequence
<220> FEATURE:
<223> OTHER INFORMATION: Mutant polymerase sequence motif
<220> FEATURE:
<221> NAME/KEY: VARIANT
<222> LOCATION: (7)..(7)
<223> OTHER INFORMATION: x = S or T
<220> FEATURE:
<221> NAME/KEY: VARIANT
<222> LOCATION: (8)..(8)
<223> OTHER INFORMATION: x = G, T, R, K, or L

<400> SEQUENCE: 15

Thr Gly Arg Leu Ser Ser Xaa Xaa Pro Asn Leu Gln Asn
1               5                   10
```